United States Patent [19]

Gouinlock, Jr. et al.

[11] 4,051,106
[45] Sept. 27, 1977

[54] HIGH MOLECULAR WEIGHT COPOLYESTER RESINS HAVING A HIGH DEGREE OF ALTERNATING STRUCTURE

[75] Inventors: Edward V. Gouinlock, Jr., Warsaw; Jerold C. Rosenfeld, Tonawanda, both of N.Y.

[73] Assignee: Hooker Chemicals & Plastics Corporation, Niagara Falls, N.Y.

[21] Appl. No.: 542,637

[22] Filed: Jan. 20, 1975

[51] Int. Cl.² .................... C08G 63/18; C08G 63/42
[52] U.S. Cl. .................................. 260/47 C; 260/860
[58] Field of Search ................... 260/47 C, 75 M, 860

[56] References Cited

U.S. PATENT DOCUMENTS

| 3,398,120 | 8/1968 | Hindersinn et al. ............... 260/47 C |
| 3,471,441 | 10/1969 | Hindersinn ......................... 260/47 C |
| 3,498,950 | 3/1970 | Shatz et al. ........................ 260/47 C |
| 3,702,838 | 11/1972 | Wilson ............................... 260/47 C |

FOREIGN PATENT DOCUMENTS 1,390,699   1/1965   France

*Primary Examiner*—V.P. Hoke
*Attorney, Agent, or Firm*—Peter F. Casella; James F. Mudd

[57] ABSTRACT

High molecular weight, linear aromatic polyesters having a very high degree of alternating microstructure are produced by reacting a hydroxyl-containing component with an excess of acid halide, recovering the bis adduct thus formed and thereafter polymerizing the bis adduct with additional hydroxy-containing components.

11 Claims, No Drawings

HIGH MOLECULAR WEIGHT COPOLYESTER RESINS HAVING A HIGH DEGREE OF ALTERNATING STRUCTURE

BACKGROUND OF THE INVENTION

High molecular weight linear polyester compositions based on bisphenols have been known to be useful in the preparation of films and fibers. These compounds, when molded into useful articles using conventional techniques, offer properties superior to those articles molded from other linear polyester compositions.

Bisphenol polyesters can be prepared by three condensation techniques, i.e., melt, homogeneous, and interfacial condensation techniques. Melt or bulk polymerization is the simplest method and in this technique, generally the reactants and catalysts are charged into a vessel and heated under vacuum. High temperatures are required and high viscosities encountered. Homogeneous or solution polymerization generally offers the advantage of being able to run the polymerization reaction at moderate temperatures and viscosities due to the presence of the solvent and catalyst. Disadvantages include necessity to remove solvent and low yield reactor volume. In the interfacial method, the reactants are dissolved in solvents which are immiscible with each other and their reaction takes place at the interface of the solvent. Advantages and disadvantages are generally similar to the solution polymerization process.

Whichever of the three condensation techniques are employed, the linear aromatic polyester produced is essentially a random polymer. As the condensation reaction proceeds, a mixture of dimers, trimers, tetramers, etc., are produced resulting in the product having an essentially random polymer characterized by an alternating microstructure of about 50%.

In the solution condensation of a bisphenol and an aromatic dicarboxylic acid halide, it is known to add the dihalide to the bisphenol or glycol or to mix the two reactants followed by addition of a suitable catalyst, and in both instances to initially employ one diol so as to form a prepolymer and thereafter add the second diol. See, e.g., Korshak et al, J. Poly. Sci., A-1, 11, 2209 (1973). The addition of the aromatic dicarboxylic acid halide to the hydroxyl-containing component is standard procedure. Copending application Serial No. 542,636 filed of even date herewith, discloses that adding the hydroxyl-containing component sequentially to the diacid halide in solution polymerization surprisingly produces high molecular weight copolyesters which have a relatively low melt viscosity and a higher degree of alternating microstructure than conventional polyesters.

This application is similar to the copending application in that a sequential addition of reactants is utilized and high molecular weight copolyesters are obtained. However, the process of this invention is not restricted to solution polymerization and the polyester produced has a significantly higher degree of alternating microstructure and a significantly higher melt viscosity compared to the products of the copending application. Thus, while the products of the copending application are useful in extrusion molding, the products of the present invention are not amenable to extrusion molding but instead can be solvent cast by techniques well known to those skilled in the art.

Accordingly, it is the object of this invention to provide a new process for the production of novel high molecular weight aromatic copolyesters having a high degree of alternating microstructure and also to provide new high molecular weight aromatic copolyesters. This and other objects of the invention will become apparent to those skilled in the art from the following detailed description.

SUMMARY OF THE INVENTION

This invention relates to a process for the production of high molecular weight, highly ordered microstructure, linear aromatic polyesters by adding a hydroxyl-containing component to an excess of diacid halide to form a bis adduct, separating all or part of the unreacted diacid halide from the bis adduct and thereafter reacting the bis adduct or bis adduct admixture with diacid halide with a different hydroxyl-containing material, and also to the novel polyesters thus produced. An amount of a different diacid halide can be added to the bis adduct before proceeding with the reaction with the second hydroxyl-containing component.

DESCRIPTION OF THE PREFERRED EMBODIMENTS

The process of the present invention involves two separate, albeit similar, condensations of acid and hydroxyl components to produce the novel high molecular weight linear aromatic polyesters. In the first condensation, a bis adduct (acid dimer) or bis adduct admixture with diacid halide is produced which is then used in the second condensation reaction. The first condensation can be performed by either the melt or solution techniques. The second condensation reactions can be performed by either the melt, solution or interfacial techniques. The condensation technique employed in one stage is not dependent on the condensation technique used in the other condensation stage. In other words, the condensation technique employed in the first condensation reaction may be the same or different from the condensation technique used in the other condensation reaction. The three condensation techniques are well known and will not be described in any detail here.

The diacid halides which can be used in the present invention include oxalyl chloride and diacid halides of the formula

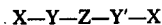

wherein Z is a bivalent or disubstituted radical of 1 to about 20 carbon atoms selected from the group consisting of alkylene, arylene, cycloalkylene, alkylarylene, and arylene-B-arylene where B is —O—, —S—, —SO—, —SO$_2$—, —SO$_3$—, —CO—,

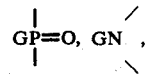

or alkylene; Y and Y' are independently selected from the group consisting of CO, SO, SO$_2$; and X is halogen. G is defined hereinafter with respect to the bisphenols. Additionally, mixtures of the diacid halides may be employed to achieve a polymer with especially desired properties.

Among aromatic disulfonyl halides which can be used in the polycondensation reaction according to the invention are: 1,4-benzene disulfonyl chloride; 1,3-benzene disulfonyl chloride; 1,2-benzene disulfonyl chloride; 2,7-naphthalene disulfonyl chloride; 4,4'-diphenyl disulfonyl chloride; 4,4'-diphenyloxide disulfonyl chloride; 4,4'-diphenylmethane disulfonyl chloride; 4,4'-diphenylsulfone disulfonyl chloride; 3,3'-diphenylsulfone disulfonyl chloride; bis-(4-chlorosulfonylphenyl)-2,2'-propane; 4,5-dichloro-1,3-benzene disulfonyl chloride; 4,6-dichloro-1,3-benzene disulfonyl chloride; and 4,5,6-trichloro-1,3-benzene disulfonyl chloride.

Among the diacid halides of dicarboxylic acids which can be used according to the invention are: terephthaloyl chloride; isophthaloyl chloride; sebacoyl chloride; adipoyl chloride; 4,4'-diphenylether dicarboxylic acid chloride; fumaryl chloride; and maleoyl chloride.

Diacid halides of aromatic monocarboxysulfonic acids include m-chlorosulfonylbenzoyl chloride; p-chlorosulfonylbenzoyl chloride; and 2-sulfonylchloride-1-naphthyl chloride.

Other typical examples include the acid chlorides of bis(4-carboxyphenyl)-sulfone; bis(4-carboxyphenyl)-carbonyl; bis(4-carboxyphenyl)-methane; bis(4-carboxyphenyl)-dichloromethane; 1,2- and 1,1-bis(4-carboxyphenyl)-ethane; 1,1- and 2,2-bis(4-carboxyphenyl)-propane; 1,1-and 2,2-bix(3-carboxyphenyl)-propane; 2,2-bis(4-carboxyphenyl)-1,1-dimethyl-propane; 1,1- and 2,2-bis(4-carboxyphenyl)-butane; 1,1- and 2,2-bis(4-carboxyphenyl)-pentane; 3,3-bis(4-carboxyphenyl)-heptane; 3,3-bis(3-carboxyphenyl)-heptane and bis (4-carboxy)diphenyl.

Although the preferred chlorides have been listed above, the other halides, especially the bromides but also the fluorides and iodides, may be suitably substituted for the chlorides to obtain good results.

When polymers of the invention having high percentage alternating structure are desired, the acid halide preferably should be one which is capable of transmitting inductive effects. In such an acid halide, when one acid halide group reacts with a diol, the reactivity of the second acid halide group changes. Such acid halides are those of the formula wherein Z is arylene or alkylarylene. Also useful are oxalyl chloride, fumaryl chloride and maleoyl chloride.

The hydroxyl-containing component used in the present invention is a mixture of a bisphenol and a glycol or a mixture of two different bisphenols or a mixture of two different glycols.

The bisphenols considered useful for the preparation of high molecular weight polyesters according to the present invention correspond to the general formula:

$$HO-Ar-E_d-Ar-OH$$
$$\phantom{HO-Ar-}T_b\phantom{-}G_m\phantom{-}T_b$$

wherein Ar is aromatic, preferably containing 6–18 carbon atoms (including phenyl, biphenyl and naphthyl), G is selected from the group consisting of alkyl, aryl, haloaryl, haloalkylaryl, alkylaryl, cycloalkyl, halocycloalkyl, and haloalkyl, and suitably containing 1–14 carbon atoms; E is a bivalent (or disubstituted) radical selected from the group consisting of alkylene, haloalkylene, cycloalkylene, halocycloalkylene, arylene, haloarylene, —O—, —SO—, —SO$_2$—, —SO$_3$—, —CO—,

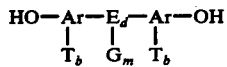

and preferably contains 1–14 carbon atoms; T is selected from the group consisting of halogen, G or OG, Cl and Br being preferred halogens; m is 0 to the number of replaceable hydrogen atoms on E; b is 0 to the number of replaceable hydrogen atoms on Ar; and d is 0 or 1. When there is a plurality of G and T substituents in the bisphenols according to the above formula, these substituents may be the same or different. The T substituents may occur in the ortho-, meta-, or para-position with respect to the hydroxyl radical. Additionally, mixtures of the above described bisphenols may be employed to achieve a polymer with especially desired properties. The bisphenols can contain 12 to about 30 carbon atoms, preferably 12 to about 25 carbon atoms.

Bisphenols having the above general formula and which are suitable for being applied according to the present invention include, but are not limited to, bis(4-hydroxyphenyl)-methane, bis(3-methyl-4-hydroxyphenyl)-methane, bis(4-hydroxy-3,5-dichlorophenyl)-methane, bis(4-hydroxy-3,5-dibromophenyl)-methane, bis(4-hydroxy-3,5-difluorophenyl)-methane, bis(4-hydroxyphenyl)-2,2-propane, bis(3-chloro-4-hydroxyphenyl)-2,2-propane, bis(4-hydroxy-3,5-dichlorophenyl)-2,2-propane, bis(4-hydroxynaphthyl)-2,2-propane, bis(4-hydroxyphenyl)-phenylmethane, bis(4-hydroxyphenyl)-diphenylmethane, bis(4-hydroxyphenyl)-4'-chlorophenylmethane, bis(4-hydroxyphenyl)-2,2,2-trichloro-1,2-ethane, bis(4-hydroxyphenyl)-1,1-cyclohexane, bis(4-hydroxyphenyl)-cyclohexylmethane, 4,4'-dihydroxydiphenyl, 2,2'-dihydroxydiphenyl, dihydroxynaphthalene, bis(4-hydroxyphenyl)-2,2-butane, bis(3,5-dichloro-4-hydroxyphenyl)-2,2-propane, bis(2-methyl-4-hydroxyphenyl)-2,2-propane, bis(3-methyl-4-hydroxyphenyl)-1,1-cyclohexane, bis(2-hydroxy-4-methylphenyl)-1,1-butane, bis(2-hydroxy-4-tertbutylphenyl)-2,2-propane, bis(4-hydroxyphenyl)-1-phenyl-1,1-ethane, 4,4'-dihydroxy-3-methyldiphenyl-2,2-propane, 4,4'-dihydroxy-3-methyl-3'-isopropyldiphenyl-2,2-butane, bis(3,5-dibromo-4-hydroxyphenyl)-phenyl phosphine oxide, bis(4-hydroxyphenyl)-sulfoxide, bis(4-hydroxyphenyl)-sulfone, bis(4-hydroxyphenyl)-sulfonate, bis(4-hydroxyphenyl)-sulfide, bis(4-hydroxyphenyl) methyl-amine, 2,3,5,6,2',3',5',6'-octachloro-4,4'-hydroxy-biphenyl, and bis(3,5-dibromo-4-hydroxyphenyl)-ketone and bis(3,5-dibromo-4hydroxyphenyl)-2,2-propane.

In addition to the above recited para hydroxy bisphenols, the corresponding ortho and meta hydroxy bisphenols can be employed in the process of this invention.

The bisphenols and glycols can be employed in proportions from 0 to 100 percent of either, as long as two different compounds are employed. The glycol is preferably employed in any amount from 5 up to about 95 mol percent of the hydroxyl-containing component with the bisphenol constituting the balance. More preferably, the diol is 15-85 mol percent of the hydroxyl-containing component and most preferably about 50 mol percent. In general, the glycols will contain 2-40 carbon atoms and typical examples include ethylene glycol, diethylene glycol, triethylene glycol, tetraethylene glycol, propylene glycol, dipropylene glycol, polypropylene glycol, hexylene glycol, 2-methyl-2-ethyl- 1,3-propanediol, 2-ethyl-1,13-hexanediol, 1,5-pentanediol, thiodiglycol, 1,3-propanediol, 1,3-butanediol, 2,3-butanediol, 1,4-butanediol, 1,3-butylene glycol, neopentyl glycol, 1,2-dimethyl-1,2-cyclopentanediol, 1,2-cyclohexanediol, 1,2-dimethyl-1,2-cyclohexanediol, 2,2,4-trimethyl-1,3-pentanediol, polyethylene glycol, hydroxyl-terminated aliphatic polyesters of, e.g., about 1000 molecular weight, and the like.

When the condensation technique employed normally entails use of a catalyst, any of those materials which are known to be catalysts for the condensation reaction can be employed in this invention. Such catalysts are bases, such as tertiary amines such as trimethylamine, triethylamine, pyridine and the like. The base catalyzes the reaction and also appears to neutralize the hydrogen chloride that would otherwise be liberated during the condensation reaction. The catalyst (and HCl acceptor) is usually employed in twice the molar quantity of the diacid halide although a slight excess of up to about 15 molar percent, preferably 5-10 molar percent, is generally employed to ensure completeness of reaction and to compensate for any loss of volatile base. In many cases, the glycol and diacid halide can be reacted thermally without a catalyst.

The highly ordered microstructure polyesters of the present invention are obtained by employing a stoichiometric excess of the diacid halide in the first condensation reaction of this invention. The molar ratio of diacid halide to hydroxyl-containing component can range from 3:1 to about 100:1 and is preferably about 15:1 to 20:1. It is important to maintain the diacid halide in excess throughout this first condensation reaction and therefore the hydroxyl-containing component is added to the diacid halide regardless of which polycondensation technique is being utilized.

By carrying out the initial condensation reaction in this fashion, a bis-structured adduct of 2 mols of the diacid halide interconnected by 1 mol of the hydroxyl-containing component is formed. In order to obtain the high degree of alternating structure which characterizes the polyesters of this invention, it is important at this point in the reaction sequence to remove part or all of the excess diacid halide from the bis-adduct. This can be conveniently accomplished by stripping off the excess diacid halide under vacuum although other techniques apparent to those skilled in the art can also be used. The second condensation reaction of this invention is essentially the known polycondensation reaction except that the acid dimer or dimer mixture recovered from the initial condensation reaction is used as the acid component. If desired, additional amounts of any of the same or other diacid halides can be used in conjunction with the bis-adduct as the acid component. It is also preferred to add the hydroxyl-containing component to the acid component in the second condensation reaction.

As an example of the sequential technique of the present invention, a diol such as neopentyl glycol can be added to an excess of terephthaloyl chloride and the reaction continued until all of the HCl has evolved thereby forming a dimer of the formula

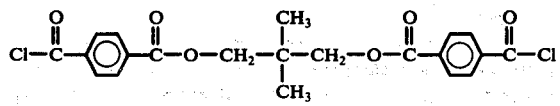

and after the excess terephthaloyl chloride has been stripped off under vacuum, a sufficient stoichiometric amount of bisphenol-A is added to the adduct. The resulting polyester has a high molecular weight, a high melt viscosity and a very high percentage of alternating microstructure.

The following Examples are presented in order to further illustrate the present invention. In these Examples, as well as throughout this specification and claims, all parts and percentages are by weight, all temperatures are in degrees Centigrade, and all intrinsic viscosities were measured in 1,1,2,2-tetrachloroethane at 30° C. unless otherwise specified.

EXAMPLE 1

406 g (2.0 mols) of terephthaloyl chloride were placed in a 2-liter flask equipped with an addition funnel with a nitrogen inlet on top, and a Y tube with a thermometer and condenser. The condenser was connected to a 1-liter suction flask which contained 800 cc of stirred distilled water which served as an HCl trap. The inlet tube to the 1 liter flask is located well under the surface of the water and the water is stirred with a magnetic stirrer. The 2-liter flask was equipped with a mechanical stirrer.

10.4 g (0.10 mol) of neopentyl glycol was dissolved in 225 ml of distilled and dried methylene chloride, charged to the addition funnel, and a slow flow of dry nitrogen gas was begun. The terephthaloyl chloride was heated by means of an oil bath and the neopentyl glycol solution was added over a 1 hour period at 70°-90° C. The reaction mixture was then heated at approximately 100° C. for 2.3 hours during which time the methylene chloride and 96.8% of the theoretical HCl were removed from the reaction mixture.

The reaction mixture was allowed to cool under nitrogen and the condenser replaced by a Vigreaux column and distillation head with vacuum take-off and receiver. The unreacted terephthaloyl chloride was removed under vacuum (less than 1 mm Hg) at about 150° C. for about 1.2 hours leaving 42.5 g of a diacid halide adduct. The adduct was then transferred to a clean 2-liter Morton flask by dissolving and rinsing the dimer with 500 cc of methylene chloride.

A solution of 23.5 g (0.103 mol) bisphenol-A, 10.6 g (0.268 mol) sodium hydroxide (pellets) and 200 ml distilled water was prepared and charged to an addition funnel which had been placed on the Morton flask. 1.25 g of a 60% aqueous solution of benzyl trimethyl ammonium chloride was added to 41.5 ml distilled water, was poured into the Morton flask, rapid stirring begun, and addition of the bisphenol-A solution begun immediately and completed in 30 minutes without either heating or cooling. The reaction mixture was allowed to stir for several hours and then 15 ml of concentrated aqueous HCl was added and stirring continued for an additional hour. The methylene chloride-polymer solution was then diluted further with additional methylene chloride and washed with distilled water in a separatory funnel until the washings were free of chloride ion by the silver nitrate test (11 washings). The polymer was recovered by dripping the solution into hot, rapidly stirred, water in a blender. The polymer was then dried in vacuum at approximately 100° C. The intrinsic viscosity of the polymer in tetrachloroethane at 30° C. was 1.61. The polymer had a number average molecular weight of 37,600 and a weight average molecular weight of 175,000. The percentage of alternating structure, as measured by 220 MH, NMR analysis was 92±2%.

Moldings were prepared on a Custom Scientific Instruments Mini Max Molder and were opaque. The microtensile impact strength as measured on a Custom Scientific Instruments impact tester was ≧9.3 inch-pounds.

EXAMPLE 2

For comparative purposes, Example 1 was repeated except that the molar ratio of terephthaloyl chloride to neopentyl glycol was 2:1; that the first condensation reaction was effected in a resin kettle and the second condensation reaction in a 10 gallon glass lined reactor, and that the terephthaloyl chloride was not removed at the end of the first condensation reaction. In addition, in the first stage, the neopentyl glycol and terephthaloyl chloride were charged initially to the flask and heated at about 100° C., i.e., no solvent is used. The final polymer was isolated by precipitation into acetone and exhibited an intrinsic viscosity in methylene chloride at 30° C. of 0.80. Moldings prepared on a Custom Scientific Instruments Mini Max Molder were clear. The microtensile impact strength as measured on a Custom Scientific Instruments impact tester was ≧11.5 inch-pounds.

The comparison between the polymers of Examples 1 and 2 is:

| Example | 1 | 2 |
|---|---|---|
| % Alternating Microstructure | 92 | 48.5 |
| $(\eta)^*$ | 0.69 | 0.75 |
| Viscosity, Poise, 300° C | 114,000 | 97,000 |
| Viscosity, Poise (extrapolated to $(\eta)$ = 0.700, 300° C | 119,000 | 54,000 |

*determined on extrudate from melt viscometer with barrel at 300° C.

EXAMPLE 3

The preparation of the bis adduct and stripping of the excess terephthaloyl chloride as described in Example 1 was repeated. The isolated adduct was then transferred to a 1-liter flask with 400 cc of dry methylene chloride. 0.1 mol bisphenol-A and 0.11 mol triethylamine and 300 ml methylene chloride were added to the adduct solution through an addition funnel over a 1 hour period at 20°-25° C. with stirring and the resulting mixture stirred for an additional hour. Thereafter, 10 ml of concentrated aqueous HCl was added and the mixture stirred for 15 minutes. The polymer-methylene chloride solution was washed with distilled water until chloride-free and the polymer recovered by dripping the solution into a stirred blender filled with hot water. The resulting polymer had a high molecular weight and a high degree of alternating structure.

EXAMPLE 4

The preparation of the bis adduct and stripping of excess terephthaloyl chloride as described in Example 1 is repeated. 0.1 mol bisphenol-A is added to the bis adduct. The mixture is reacted thermally with removal of HCl under nitrogen and a vacuum until a high molecular weight polymer is obtained.

EXAMPLE 5

Example 1 is repeated using 2.0 mols of isophthaloyl chloride in place of the terephthaloyl chloride to obtain a high molecular weight, highly ordered microstructure polyester.

EXAMPLE 6

Example 1 is repeated using a mixture of 1.0 mol of terephthaloyl chloride and 1.0 mol of isophthaloyl chloride in place of the terephthaloyl chloride to obtain a high molecular weight, highly ordered microstructure polyester.

EXAMPLE 7

Example 1 is repeated using 0.05 mol bisphenol-A in place of part of the neopentyl glycol to obtain a high molecular weight, highly ordered microstructure polyester.

EXAMPLE 8

Example 1 is repeated using 0.1 mol ethylene glycol in place of the neopentyl glycol to obtain a high molecular weight, highly ordered microstructure polyester.

The novel polyesters prepared according to this invention are generally characterized by having an intrinsic viscosity of at least about 0.4 dl/g in symmetrical tetrachloroethane at 30° C, preferably at least about 0.6 dl/g and more preferably at least about 0.7 dl/g. The polyesters also have a relatively high degree of alternating structure compared to polyesters made by processes that produce products having a random structure. In the working examples provided herein, the amount of alternating structure is expressed as a percentage determined by NMR. The extent or degree of alternating structure has been expressed in the literature (See Yamadera et al, J. Poly. Sci., A-1, 5 2259-2268 (1967), as a B value for polymers produced from a 50:50 mixture of two different hydroxyl components (such as 0.5 mole fraction of bisphenol A and 0.5 mole fraction of ethylene glycol). The B value is two times the percent alternating structure divided by 100. (Thus, the B value for the polymer of Example 1 herein is 1.84). The degree of alternating structure irrespective of the mole fractions of the hydroxyl containing component can be expressed as an Alternation Index (A) which is defined as follows:

$$A = 1 + \left( \frac{b_f - b_r}{b_m - b_r} \right)$$

wherein
  $b_f$ is the mole fraction of alternating copolymer structure found in the polymer by NMR.
  $b_r$ is the mole fraction of alternating copolymer structure that would be produced by a reaction that produces random structure.
  $b_m$ is the maximum mole fraction of alternating copolymer structure that is theoretically possible.

A polymer having all alternating structure has an A value of 2.0; a polymer having all random structure has an A value of 1.0, while a polymer having completely block structure has an A value of 0. The novel polymers produced in accordance with this invention have an Alternation Index of about 1.6, preferably at least about 1.7 up to 2.0.

Various changes and modifications can be made in the process of this invention without departing from the spirit and the scope thereof. For example, and as illustrated in the Examples, by taking advantage of reactivity ratio differences or different monomers (See Vinogradova et al, Vyskimol Soed., pp 457-462 (1972) by, e.g. varying addition order and ratios, not only high molecular weight linear copolyesters but also terpolymers, etc., can be prepared. Accordingly, it will be understood that the various embodiments disclosed herein were for the purpose of further illustrating the invention but were not intended to limit it.

Various changes and modifications can be made in the process of this invention without departing from the spirit and the scope thereof. The various embodiments described herein were for the purpose of further illustrating the invention but were not intended to limit it.

We claim:

1. A process for the production of high molecular weight, linear aromatic polyesters having an alternation index above 1.6 by reacting an organic diacid halide with a hydroxyl-containing component comprising a combination of a bisphenol and 5 to 95 mol percent of a glycol, said process comprising:
   a. adding one member of the combination of a hydroxyl-containing component to the diacid halide employing at least 3 mols of diacid halide per mol of hydroxyl-containing component,
   b. reacting the resulting mixture so as to form a bis-adduct,
   c. removing all of the unreacted diacid halide from the bis-adduct, and
   d. thereafter reacting the bis-adduct with a different member of the combination of hydroxyl-containing component so as to form the desired high molecular weight linear polyester, and wherein the diacid halide is terephthaloyl chloride, isophthaloyl chloride or a mixture thereof, the glycol has 2-20 carbon atoms, and the bisphenol has the formula

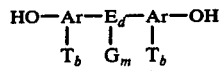

in which Ar is aromatic, each T is independently selected from the group consisting of halogen, G or OG, each G is independently selected from the group consisting of alkyl, aryl, haloaryl, haloalkylaryl, alklaryl, cycloalkyl, halocycloalkyl, and haloalkyl, E is a bivalent alkylene, haloalkylene, cycloalkylene, halocycloalkylene, arylene, haloarylene, —O—,—S—,—SO—,—SO₂—,—SO₃—, —CO—,

or GN<, $m$ is 0 to the number of replaceable hydrogen atoms on E, each $b$ is 0 to the number of replaceable hydrogen atoms and $d$ is 0 or 1.

2. The process of claim 1 wherein the molar ratio of diacid halide to hydroxyl-containing component in (a) is 3:1 to about 100:1.

3. The process of claim 2 wherein the molar ratio is 15:1 to 20:1.

4. The process of claim 2 wherein in said bisphenol formula, Ar contains 6-18 carbon atoms, G contains 1-14 carbon atoms, and E contains 1-14 carbon atoms; and wherein said glycol is 15-85 mol percent of the hydroxyl-containing component.

5. The process of claim 2 wherein; in said bisphenol formula, Ar is phenyl, E is alkylene, G is alkyl, $d$ is 1, and $m$ is 2.

6. The process of claim 5 wherein said glycol is neopentyl glycol or ethylene glycol 7. A linear aromatic polyester of components comprising an organic diacid halide and a hydroxyl-containing component comprising a combination of a bisphenol and 5 to about 95 mol percent of a glycol, said polyester having an intrinsic viscosity of at least about 0.6 dl/g in tetrachloroethane at 30° C. and an alternation index of above 1.6 and wherein the diacid halide is terephthaloyl chloride, isophthaloyl chloride or a mixture thereof, the glycol has 2-20 carbon atoms, and the bisphenol has the formula

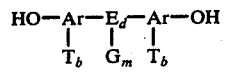

in which Ar is aromatic, each T is independently selected from the group consisting of halogen, G and OG, each G is independently selected from the group consisting of alkyl, aryl, haloaryl, haloalkylaryl, alklaryl, cycloalkyl, halocycloalkyl, and haloalkyl, E is a bivalent alkylene, haloalkylene, cycloalkylene, halocycloalkylene, arylene, haloarylene, —O—, —S—, —SO—, —SO₂—, —SO₃—, —CO—,

or GN<, $m$ is 0 to the number of replaceable hydrogen atoms on E, each $b$ is 0 to the number of replaceable hydrogen atoms on Ar, and $d$ is 0 or 1.

8. A high molecular weight, linear aromatic polyester of components comprising an organic diacid halide and a hydroxyl-containing component comprising a combination of a bisphenol and 15 to 85 mol percent of a glycol, said polyester having an intrinsic viscosity of at least about 0.6 dl/g in tetrachloroethane at 30° C. and alternation index of above 1.6, and wherein the diacid halide is terephtaloyl chloride, isophthaloyl chloride of a mixture thereof, the glycol has 2-20 carbon atoms, and the bisphenol has the formula

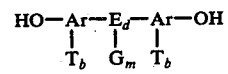

in which Ar is aromatic, each T is independently selected from the group consisting of halogen, G or OG, each G is independently selected from the group consisting of alkyl, aryl, haloaryl, haloalkyaryl, alkylaryl, cycloalkyl, halocycloalkyl, and haloalkyl, E is a bivalent alkylene, haloalkylene, cycloalkylene, halocycloalkylene, arylene, haloarylene, —O—, —S—, —SO—, —SO₂—, —SO₃—, —Co—,

or GN<, $m$ is 0 to the number of replaceable hydrogen atoms on E, each $b$ is 0 to the number of replaceable hydrogen atoms on Ar, and $d$ is 0 or 1.

9. The polyester of claim 8 having an intrinsic viscosity of at least about 0.7 dl/g in sym-tetrachloroethane at 30° C and an alternation index of at least about 1.7.

10. The polyester of claim 9 of ingredients comprising at least one of terephthaloyl chloride and isophthaloyl chloride, and 15-85 mol percent bisphenol-A and 85-15 mol percent of a 2-20 atom glycol.

11. The polyester of claim 10 wherein the glycol is neopentyl glycol.

* * * * *

UNITED STATES PATENT OFFICE
CERTIFICATE OF CORRECTION

Patent No. 4,051,106　　　　　　　　Dated September 27, 1977

Inventor(s) Edward V. Gouinlock, Jr., et al.

It is certified that error appears in the above-identified patent and that said Letters Patent are hereby corrected as shown below:

At Column 3, line 67, for "-O-, -SO-", read "-O-, -S-, -SO-".

At Column 4, line 28, for "bis(4-hydroxyphenyl)-2,2-propane," read "bis(4-hydroxyphenyl)-2,2-propane /̄common name - bisphenol-A_/".

At Column 7, line 6, for "　9.3", read "　9.3".

At Column 7, line 26, for "　11.5", read "　11.5".

At Column 7, line 35, for "0.700," read "0.70),".

At Column 9, line 2, for "Vyskimol" read "Vysokimol".

At Column 9, line 47, for "alklaryl" read "alkylaryl".

At Column 9, line 60, for "hydrogen atoms and d", read "hydrogen atoms on Ar, and d".

At Column 10, line 26, for "alklaryl" read "alkylaryl".

At Column 10, line 47, for "of" read "or".

At Column 10, line 58, for "haloalkyaryl" read "haloalkylaryl".

UNITED STATES PATENT OFFICE

CERTIFICATE OF CORRECTION

Patent No. 4,051,106　　　　　　　　Dated September 27, 1977

Inventor(s) Edward V. Gouinlock, Jr., et al.

It is certified that error appears in the above-identified patent and that said Letters Patent are hereby corrected as shown below:

At Column 10, line 47, for "terephtaloyl" read "terephthaloyl",

At Column 10, line 62, for "-Co-", read "-CO-".

Signed and Sealed this

*Twenty-fourth* Day of *July 1979*

[SEAL]

*Attest:*

*Attesting Officer*　　　　　　　　LUTRELLE F. PARKER
　　　　　　　　*Acting Commissioner of Patents and Trademarks*